United States Patent [19]
Laghi

[11] Patent Number: 5,061,284
[45] Date of Patent: Oct. 29, 1991

[54] SILICONE FOLLICLED HAIR IMPLANT

[76] Inventor: Aldo A. Laghi, 13 Meridian La., Ballston Lake, N.Y. 12019

[21] Appl. No.: 507,356

[22] Filed: Apr. 10, 1990

[51] Int. Cl.$^5$ .............................................. A61F 2/10
[52] U.S. Cl. ........................................ 623/15; 623/11; 132/201
[58] Field of Search ........................ 623/1, 11, 12, 15; 132/53, 201

[56] References Cited

U.S. PATENT DOCUMENTS

| | | | |
|---|---|---|---|
| 3,003,155 | 10/1961 | Mielzynski | 3/1 |
| 3,119,398 | 1/1964 | Bennett et al. | 132/201 |
| 3,460,975 | 8/1969 | Stebleton | 623/11 |
| 4,517,997 | 5/1985 | Forchetti | 132/5 |
| 4,947,877 | 8/1990 | Meyer et al. | 132/201 |
| 4,969,903 | 11/1990 | Valle | 623/15 |

FOREIGN PATENT DOCUMENTS 3011520 10/1980 Japan ................................. 132/201

*Primary Examiner*—Randall L. Green
*Assistant Examiner*—Paul Prebilic
*Attorney, Agent, or Firm*—Schmeiser, Morelle & Watts

[57] ABSTRACT

Artificial human hair follicles which encapsulate human hair ends and used for hair implantation. Human hairs are cleansed, the ends are then primed with a suitable silicone primer and up to two coatings are provided in order to form thereon a human hair follicle emulation that will be effacatious for the implantation of the treated hairs into the human derma. The artificial follicled human hairs may be implanted individually or in bundles of up to fourteen hairs with each hair strand and each bundle provided with a follicle-emulating bulbous root. In the preparation protocol, a single hair strand is first cleansed, the end is primed to receive a silicone polymer coating, a first coating is applied and before complete cure of the first coating, a second coating comprising a bulbous silicone elatomeric follicle is applied in such a fashion that the first coating will extend for a predetermined distance beyond the artificial follicle. The extension is noteworthy in that it precludes the destruction of the hair shaft by proteins inherent in the derma.

10 Claims, 1 Drawing Sheet

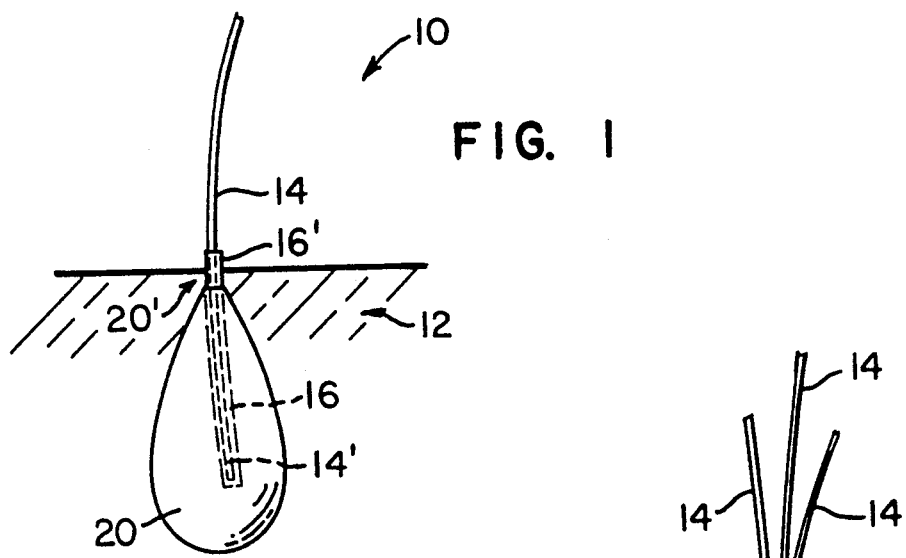
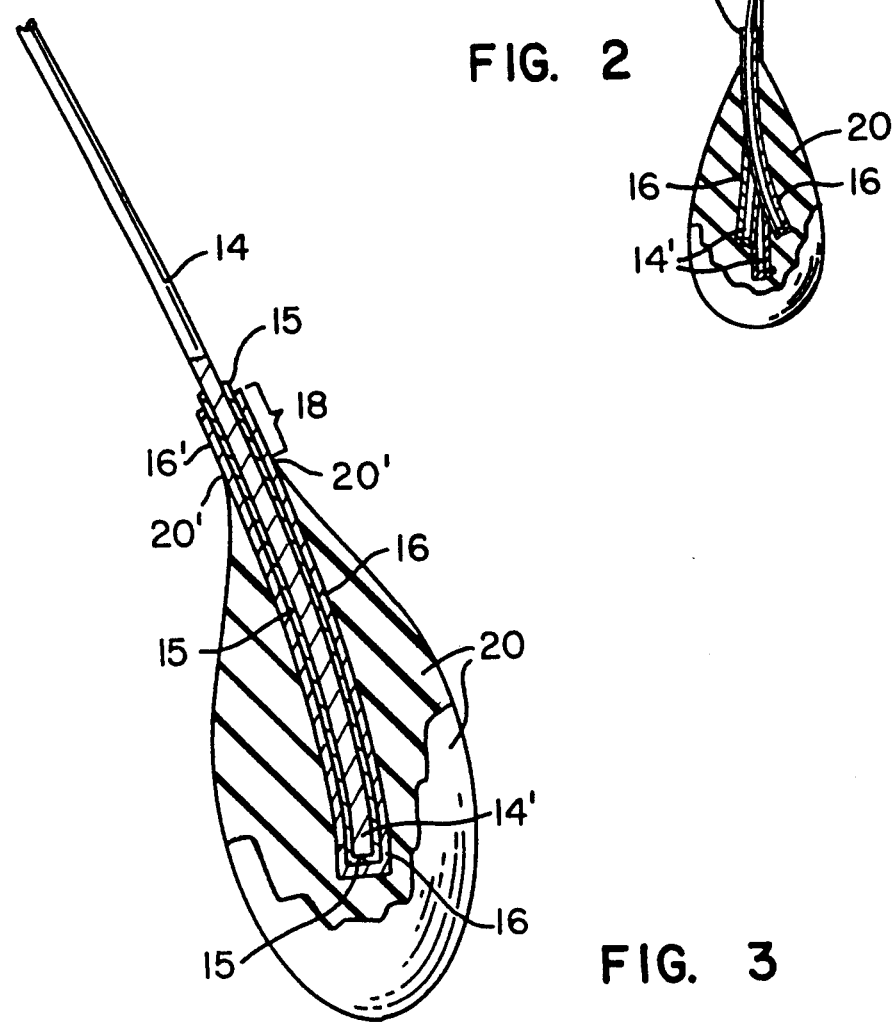

SILICONE FOLLICLED HAIR IMPLANT

BACKGROUND OF THE INVENTION

1. Field Of The Invention

This invention relates to improved human hair anchoring means such as may be implanted in the scalp of a hair implant recipient, and more specifically it pertains to the preparation of a recipient's hair, or a donor's hair, with an artificial follicle which comprises a bulbous silicone elastomer coating and a follicle extension of silicone polymer coating.

2. Description Of The Prior Art

For years costly attempts have been made to provide a viable and lasting solution to the loss of human hair. Aside from the use of toupees and wigs, or the oftentimes more questionable use of ungents and hair restoratives, surgical implantation of hair, both human and artificial, has met with varying degrees of success. In many cases, the implanted hair, if human (some methods for its implantation are discussed hereinafter), is attacked at the derma interface by proteins that are present in the derma itself. Recent studies tend to show that this mechanism for the destruction of the hair shaft and the consequent loss of hair may be much akin to the natural process which causes the syndrome known as "male pattern baldness". Should the implant have been of artificial hair or comprise certain artificial anchoring means, the primary cause of subsequent loss has been infection because of rejection by the body's defensive mechanisms acting upon a foreign substance.

A recent patent search disclosed two documents which are relevant in light of the instant invention. The first of these is U.S. Pat. No. 4,517,997, issued to Forchetti in 1985. This patent teaches the coating of a human hair with a non-infectuous, nonbody-rejecting type of material to form an enlargement at the implantation end of the hair, an artificial follicle. The distinguishing characteristics between the Forchetti patent and the instant inventor's teachings are that Forchetti uses a natural hair that is broadened at the bottom to form a hair root or follicle-emulating terminous which is then coated with an inert material, in this case gold. In the instant invention, the first end-expanding coating is a silicone polymer. The second coating is a root-or follicle-defining coat of silicone elastomer that purposefully does not encompass the entire first coating or initial end-expanding coating. Most notable in the Forchetti teaching is the fact that the inert coating (gold) does not extend intentionally beyond the surface of the derma. The inventor is quite express in this particular facet in that he both teaches and claims an inert coating that covers an enlargement of the hair end and which is the outermost layer in the singular coating scheme. Thus, Forchetti teaches a coating of gold that must cover the entire enlarged portion of the hair.

Another relevant teaching is that of Mielzynski et al in the U.S. Pat. No. 3,003,155, which issued in October 1981. The crux of the Mielzynski teaching is basically a hair implantation dart. The dart is comprised of a polymethylmethacrylate, polyethylene, vitallium or suitable adventageous material having a body tissue compatability. Mielzynski et al do not actually teach a composition beyond the scope of those mentioned and, in 1961, the art was sorely lacking in a knowledge of what compositions had true body tissue "compatability". The basic notion of the Mielzynski et al art is to take a hair strand, whether it be a human hair or an artificial strand, and place it inside a dart, cementing it therein. When the hair is to be implanted, according to Mielzynski, in an artificial embedding material, it is just knotted generally at the end to form a ball and pressed into the artifical material. When it is to be pressed or inserted into the scalp (implantation), generally a dart having a nonretrograde motion means is employed. The nonretrograde motion means comprises either a triangular dart, a heart-shaped dart, or a harpoon head dart, i.e., one having a generally triangular shape with a series of axially spaced, concentric serrations thereon. When implanted according to the teachings of Mielzynski et al, the dart is placed into the derma and the hair protrudes therefrom, with a substantial amount of the hair shaft encircled by the derma. In this particular regard, the teachings of Mielzynski et al and Forchetti are the same. The greatest disadvantage of the latter, as well as the former art, is the likelihood that the body will reject either the anchor of Mielzynski et al (methymethacrylate or the other plastics); and, more than likely, the exposure of hair (if it is natural) to the proteins (both surface and interdermal), of the skin will attack the naked hair shaft as has been noted in studies by the instant inventor and others. Thus, in both of the aforementioned prior artform teachings, an artificial hair strand, like the artficial hair darts, is oftentimes rejected by the body's defensive mechanisms; while natural hair strands that are exposed to the proteins of the skin, are generally weakened or eroded to the extent that breakage or other forms of discontinuation (at the surface) of the skin becomes inevitable in a significant number of cases.

The instant invention avoids the shortcomings of the prior art and provides a hair strand implant with an artficial follicle that will sustain itself within the scalp by use of a truly body-compatible artificial follicle, as well as a mechanism for acquiring an invulnerability to the derma proteins.

SUMMARY OF THE INVENTION

It it well known that the technique currently in use for the restoration or implantation of natural hair comprises the removal of small plugs from the scalp of a patient who has a sufficient amount of hair remaining to allow a selective removal therefrom. Such sections of the patient's head comprise those over the ears, behind the ears and at the upper neck. The removed plugs are then inserted in those areas of the scalp which have experienced the greater or more significant hair loss and in which the scalp is the most visible, typically at the top of the head. The procedure is generally painful, and not always possible, depending on the hair loss pattern of the patient.

I have devised a hair plug that consists basically in a human hair on which an artifical follicle is formed. A hair of suitable length is cleansed and a silicone primer is applied at the hair end on all of the individual hairs that are to be used so as to promote adhesion between the hair end and a silicone coating. A light coating of a silicone polymer is then placed over the primed hair end for a predetermined length and assures that, later when the silicone elastomer follicle is placed on the hair end or bundle of hair ends, the first light coating of silicone polymer will extend a predetermined distance beyond the end of the follicle. Thus, it is the light, first coat polymer, which extends beyond the follicle, that will provide the protection against erosion or destruction of the hair shaft by skin proteins. Finally, a silicone elastomer follicle that encapsulates one end of the hair(s) and has the shape of a human follicle is formed about the hair end that has been treated with the light coating of silicone polymer as aforesaid.

Silicone hair follicles may include a single hair or bundles of four to five hairs, or even ten to twelve hairs each. The follicles completely encapsulate the ends of the hairs and also encapsulate each single hair individually in order to maximize the silicone bond strength. Each hair is individually coated with the aforesaid silicone polymer beyond the exposed hair end of the follicle in order to prevent the attack on the hair shaft by proteins present in the derma. Were this not done, such as in the cases of the prior art cited, such proteins would soon destroy or erode the hair shaft and cause the hair to break or fall off.

The advantages of my artificial follicle, with follicle extension, are many fold; but the more salient are: elimination of the painful surgical removal of plugs from hairy areas of the scalp of the patient; elimination of the need for donor areas of the scalp; reduced cost, since the entire procedure (implantation) may be done in one session rather than in several painful sessions; and elimination of the recovery period necessary to heal the donor areas of the scalp.

BRIEF DESCRIPTION OF THE DRAWINGS

Of the Drawings:

FIG. 1 is an illustration of the single strand embodiment of the invention;

FIG. 2 is an illustration, in partial section, of the multi-strand embodiment of the invention; and FIG. 3 is a detailed partial section of the FIG. 1 invention.

DETAILED DESCRIPTION OF THE PREFERRED EMBODIMENT

By reference to the aforementioned drawings, the method and apparatus realized of the instant invention 10 are hereinafter explained.

Referring more particularly now to FIG. 1, the invention 10 is illustrated with a single strand 14 of human hair bearing thereon a silicone follicle 20 inserted into the derma 12 of the scalp or recipient skin area. Coextensive the hair shaft 14, and from a cut and cleansed end 14' thereof, there is illustrated a first coating 16 comprising a mixture of silicone polymers. The first coating 16 extends from the end 14' of the hair strand up the shaft to a length to be predetermined by the user of the invention, typically to extend approximately one millimeter beyond the edge 20' of the silicone follicle 20. A portion of this extension 16' will oftentimes be within the derma while a remaining portion of it always protrudes above the skin surface.

FIG. 2 illustrates a bundling of multiple single hair strands into an alternate embodiment of the invention 10. The individual hair strands are treated in accordance with the procedure and apparatus realized in the FIG. 1 discussion but are further bundled at the so-treated ends and afforded an encapsulating follicle coating 20. As in FIG. 1, a multiplicity of hair strands 14, having been individually treated according the FIG. 1 protocol are gathered to form a bundle in which the first coating 16 of the individual strands are all coarsely aligned and closely gathered to each other. Thereafter, by methods to be hereinafter described, the silicone follicle 20 is placed over the hair ends 14' and the multi-strand embodiment is realized.

In the detailed, partially sectioned illustration of FIG. 3, the salient difference, noted over FIGS. 1 and 2, is the presence of the primer coating 15 that underlies the first coating of silicone polymer 16. Actually, after the selection and cleansing of the hair strand, the primer is the first substance to be applied to the hair shaft end. It is used in order to enhance bonding of the silicone polymers of the first coating and of the bulk of the second coating elastomeric follicules to the first-treated hair shaft ends. This is done because silicones are inherently incompatible (adhesionwise) with most other materials and, without suitable pretreatment in the way of a primer, they tend not to bond to anything without primer usage or some other adhesive promoting agent. The primer comprises an alkoxy silane monomer or polymer dissolved in toluene or any other suitable solvent. When the solvent (that the primer is in) is first applied to the hair strand, it swells the hair shaft and allows the anchoring of some of the alkoxy groups into the shaft. The nature of this bond is not well understood, but is probably due either to attraction of the electronic orbitals of the primer and those of the polar molecules present in the hair (also termed Van Der Vaals Forces), or perhaps, are actually interlockings of the molecules of the primer and those of the hair constituents. This mechanism shall be hereinafter explained in greater detail. Suffice it to say that, after the polymer is applied and hair shaft has swollen somewhat, the first polymer coating 16 is applied. The extent of the first polymer coating is such that when the silicone follicle 20 is later applied, a portion of the primer and first polymer coating will extend upward on the shaft beyond the end 20' of the follicle 20. This primer polymer solution and first coating polymer comprise the combined coating 18 which serves as the follicle 20 extension 16' that is illustrated in FIG. 3. Dimensionwise, the primer 15 and first polymer 16 coatings extend anywhere from about 2 to 6 millimeters up the hair shaft from its end 14'. Both are very thin coatings. Thereafter, the follicle, which is also a silicone polymer, is affixed to the single hair strand and, if desired, to the bundled strands, (as in FIG. 2) so that its length will be typically 0.2-5.0 millimeters and its diameter will run approximately 0.5-2.0 millimeters. Depending upon the numbers of hair strands to be bundled within a follicle, or the depth to which a particular follicle is to be implanted into the skin, the lengths and diameters of the follicles may vary; however, the follicle extension 16' comprised of the first polymer coating, must always protrude, even a fraction of a millimeter, beyond the surface of the derma in order to afford the hair strand the invention's protection (mechanism) against hair dissolving/destroying agents in the surface of the skin.

In order to recapitulate and to further disclose the type of silicone coatings to be used herein, the following matters are inculcated:

Primer

As previously mentioned, the primer is applied in order to enhance bonding of the silicone polymers of the coating and of the follicle to the hair shafts. The primer is used because silicones are inherently incompatible with most other materials and they generally require the use of a primer or some adhesive promoting agent in order to cause a bond to the other material and the silicone chosen as a coating. In the instant invention, the primer comprises an alkoxy silane monomer or polymer which is dissolved, generally, in toluene or any other suitable solvent known to those in the art. The typical formula of the silicone monomer used is:

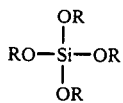

, where (OR) is an alkoxy group.

An example of the alkoxy group which is used in the instant invention is a methoxy group $CH_3O$.

Adhesion is acquired in the following fashion: the solvent containing the primer swells the hair shafts and allows the anchoring of some of the alkoxy groups into the shafts. Then, as the solvent evaporates, the alkoxy groups of the primer react with the humidity or moisture present in the air and hydrolyze according to the following mechanism:

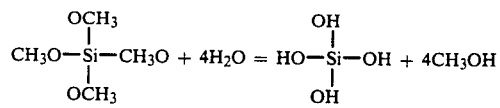

The methyl alcohol evaporates and the OH groups of the silanol monomer react with OH groups of other such molecules to form a polymer of the following type:

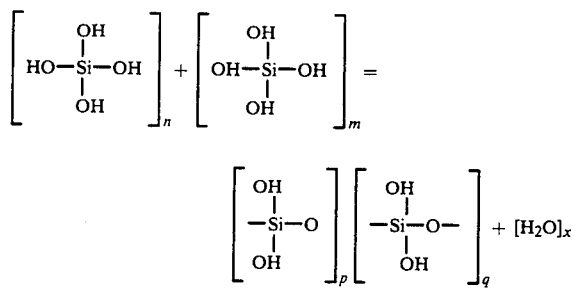

Also, OH groups still avialable for reaction along the structure of the polymer can be reacted with appropriate reactive groups of the silicone polymers which constitute the bulk of the coating 16 and of the elastomer 20 described elsewhere in this patent application.

Coating

The coating 16 comprises a mixture of silicone polymers of the following type:

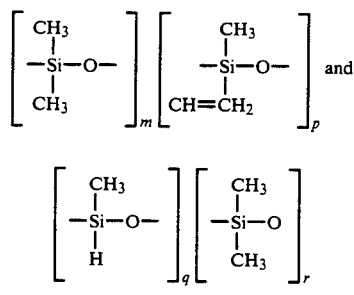

together with a few parts per million of chloroplatinic acid as catalyst.

The mixture is usually stablized at room temperature by means of a cure inhibitor such as acetylenic alcohol and dissolved in a suitable solvent such as toluene or xylene or isopropyl alcohol to reduce its viscosity.

When this mixture is applied over the primer, the —SiH groups present in the polymer of the coating 16 react with the OH groups present in the hydrolized primer 15 and provide an excellent chemical bond according to the following reactions:

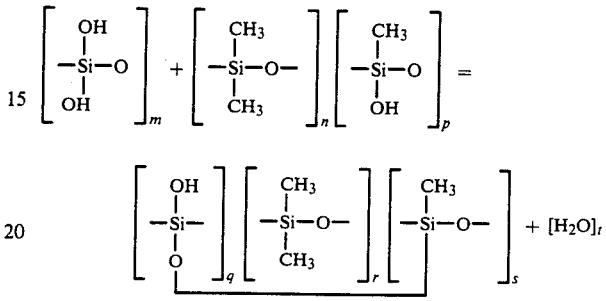

While at higher temperature, a concurrent reaction is accelerated:

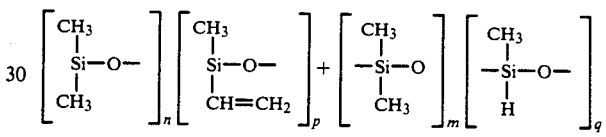

(in presence of platinum and heat):

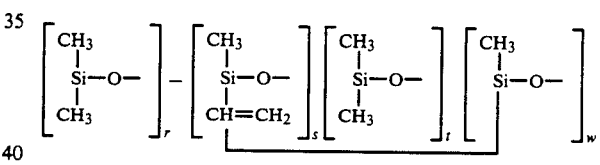

Thus, yielding a completely polymerized mass which is well bonded to the hydrolized primer, which in turn is anchored to the hair shafts.

Elastomer

The silicone polymers used for the elastomeric follicle 20 are of the same type as used for the coating. These also may be dissolved in a suitable solvent, although at a higher concentration in order to obtain a viscosity higher than that used for the coating 16. This mixture is then applied over the coating 16 before the polymerization of the coating is complete, in order to be able to react the —SiH groups present in the elastomer with the —$CH_2$=CH groups still available in the coating, and vice versa.

The method of application of the coating 16 is any of the following: dipping (which is the preferred method); flow coating; brushing; spraying; and other suitable means of applying a coating that are known in the industry. Method of applying the elastomeric follicle is similar, namely: dipping (again, the preferred method); molding; flow coating; brushing; spraying; and the like.

Thus, it may be seen that the polymers for coatings, as well as follicle construction, may be generally of the same type and applied after the same fashion. What is essential, however, is that the hair strand ends be properly cleansed and primed in order to effect not only a vehicle for silicone bonding, but a swelling of the hair ends in order to anchor some of alkoxy groups into the hair shafts. It is necessary to apply a first coating to insure that a suitable length of the hair strand end is coated in order to afford the maximum in protection of the hair shaft after it is implanted (to reside) in the recipient skin. The enlarged coating, namely the follicle 20, has as its primary purpose the bonding together of desired bunch size the invention-configured hair strands and the provision of a suitable anchor, generally of the shape that emulates a human hair follicle.

Those practicing the invention will, by continued use of the novel improvements herein, soon come to appreciate the benefits of the instant invention. Other skin-compatible and suitable silicone compositions may be used in lieu of those taught herein; however, these matters are left to those who are skilled in the art with the understanding that they shall be limited only by the hereinafter appended claims.

What is claimed is:

1. A method for preparing human hair plugs for implantation into human derma, said method comprising:
    cleaning ends of human hair strands that are to be implanted;
    disposing on each said hair end a silicone primer that will promote adhesion thereto of a silicone coating;
    coating a hair strand end that has been silicone primer coated as in the second step with a silicone polymer to a predetermined first distance extending beyond said strand end; and
    providing on said hair strand end a silicone elastomer follicle to encapsulate one or more hair ends that have been treated in accordance with the first three steps and further, by said follicle providing step, acquiring a shape of a human follicle and allowing said coating to extend a predetermined distance beyond said follicle.

2. The method of claim 1 wherein the step of coating with a silicone polymer further comprises coating a hair strand end to a first distance of up to 6.0 mm.

3. The invention of claim 2 wherein providing said follicle to encapsulate at least one or more hair ends comprises providing a bulbous follicle having outer diameter dimensions from about 0.5 mm to about 2.0 mm and length dimensions from about 2.0 mm to about 5.0 mm.

4. An artifically follicled human hair suitable for implantation into the human derma, said artifically follicled human hair comprising a human hair shaft bearing on at least one end thereof a silicone polymer primer and thereover a bulbous silicone elastomeric follicule, said follicle adheres to and encapsulates said end of both said hair shaft and primer, and further, the primer forming a hair shaft-girdling deposition which extends beyond said elastomeric follicle along said hair shaft.

5. The invention of claim 4 wherein said silicone elastomer follicle comprises silicone polymer mixtures characterized as

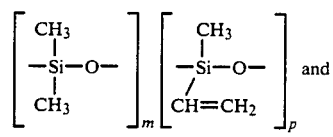

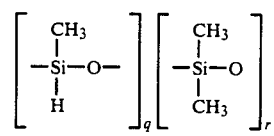

together with a few part per million of chloroplatinic acid catalyst.

6. The invention of claim 5 wherein said silicone polymer primer comprises silicone polymer mixtures characterized as

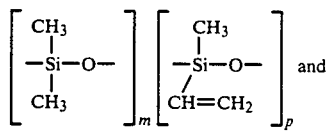

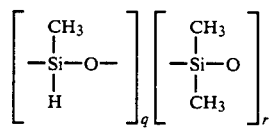

together with a few part per million of chloroplatinic acid catalyst.

7. The invention of claim 6 wherein said hair shaft girdling deposition extends beyond said follicle and about said hairshaft to a distance of about 1.0 mm.

8. The invention of claim 7 wherein said elastomer follicle has a length of from about 2.0 mm to about 5.0 mm and an outer diameter of about 0.5 mm to about 2.0 mm.

9. The invention of claim 8 wherein said elastomer follicle encapsulates more than one primer-coated human hair strand end.

10. In an implant article for replacing human hair by partial insertion of one or more said articles into a scalp, an improvement which comprises:
    at least one human hair strand, an end of which is coated with a silicone polymer primer that extends from said end to a first distance along the strand; and
    a bulbous silicone elastomeric follicle which emulates a human hair follicle and covers the strand end from a point beyond and off the end to a second distance on the strand which is short of said first distance of the primer coating.

* * * * *